US008008337B2

(12) United States Patent  (10) Patent No.: US 8,008,337 B2
Casara et al.                (45) Date of Patent:    Aug. 30, 2011

(54) AZABICYCLO[3.2.0] HEPT-3-YL COMPOUNDS, A PROCESS FOR THEIR PREPARATION AND PHARMACEUTICAL COMPOSITIONS CONTAINING THEM

(75) Inventors: Patrick Casara, Villennes sur Seine (FR); Anne-Marie Chollet, Le Pecq (FR); Alain Dhainaut, Chatou (FR); Pierre Lestage, Le Celle Saint Cloud (FR); Fany Panayi, Paris (FR)

(73) Assignee: Les Laboratoires Servier, Suresnes Cedex (FR)

( * ) Notice: Subject to any disclaimer, the term of this patent is extended or adjusted under 35 U.S.C. 154(b) by 0 days.

(21) Appl. No.: 12/928,237

(22) Filed: Dec. 7, 2010

(65) Prior Publication Data

US 2011/0136886 A1 Jun. 9, 2011

(30) Foreign Application Priority Data

Dec. 9, 2009 (FR) ...................... 09 05957

(51) Int. Cl.
 *A61K 31/403* (2006.01)
 *C07D 209/52* (2006.01)
(52) U.S. Cl. ...................... 514/412; 548/515
(58) Field of Classification Search ........................ None
 See application file for complete search history.

(56) References Cited

U.S. PATENT DOCUMENTS

2007/0197625 A1 * 8/2007 Casara et al. ................. 514/412

FOREIGN PATENT DOCUMENTS

WO  WO2005 089747  9/2005

OTHER PUBLICATIONS

French Preliminary Search Report for FR0905957 of May 26, 2010.

* cited by examiner

*Primary Examiner* — Yong Chu
*Assistant Examiner* — Michael Barker
(74) *Attorney, Agent, or Firm* — Hueschen and Sage

(57) ABSTRACT

Compounds of formula (I):

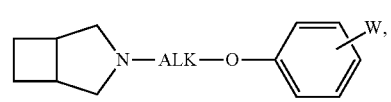

wherein:
 ALK represents an alkylene chain,
 W represents a group

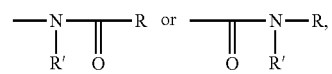

wherein R and R' are as defined in the description.
Medicinal products containing the same which are useful in the treatment of conditions associated with central histaminergic systems.

24 Claims, No Drawings

AZABICYCLO[3.2.0] HEPT-3-YL COMPOUNDS, A PROCESS FOR THEIR PREPARATION AND PHARMACEUTICAL COMPOSITIONS CONTAINING THEM

The present invention relates to new azabicyclo[3.2.0] hept-3-yl compounds, to a process for their preparation and to pharmaceutical compositions containing them.

The compounds of the present invention are especially valuable from a pharmacological point of view for their interaction with central histaminergic systems in vivo.

Ageing of the population due to increased life expectancy at birth has brought with it a large increase in the incidence of age-related neuropathologies and especially of Alzheimer's disease. The principal clinical manifestations of cerebral ageing and especially of age-related neuropathologies are deficiencies in memory and cognitive functions, which may lead to dementia.

Neuropharmacological studies have shown that, in the central nervous system, histamine, via the central histaminergic systems, has the role of a neurotransmitter or neuromodulator in physiological or physiopathological situations (Pell and Green, *Annu. Rev. Neurosci.*, 1986, 9, 209-254; Schwartz et al., *Physiol. Rev.*, 1991, 71, 1-51). Thus, it has been shown that histamine is involved in various physiological and behavioural processes, such as thermoregulation, neuro-endocrinal regulation, nociception, circadian rhythm, cataleptic states, motility, aggressiveness, eating behaviour, learning and memorisation, and synaptic plasticity (Hass et al., *Histaminergic neurones: morphology and function*, Boca Raton, Fla.: CRC Press, 1991, pp. 196-208; Brown et al., *Prog. Neurobiology*, 2001, 63, 637-672; Smith et al., *Neuroimmunomodulation* 2007, 14, pp. 317-325).

Studies carried out in animals have shown that an increase in endogenous extra-synaptic levels of histamine makes it possible to promote states of vigilance, learning and memory processes, and to regulate food intake (Brown et al., *Prog. Neurobiol.*, 2000, 63, 637-672; Passani et al., *Neurosci. Biobehav. Rev.*, 2000, 24, 107-113). As a result, the potential therapeutic indications for compounds capable of increasing the turnover or release of histamine at the central level are the treatment of cognitive deficiencies associated with cerebral ageing, with acute and chronic neurodegenerative diseases and with schizophrenia and also the treatment of mood disorders, of Tourette's syndrome (Gulhan Ercan-Sencicek et al., *New England Journal of Medicine*, May 20, 2010, 1901-1908), of schizophrenia, of sleep disorders, of sleep-waking rhythm disorders and of attention-deficit hyperactivity syndrome. Furthermore, studies have shown that an injection of histamine into the central hypothalamic nuclei involved in the regulation of satiety attenuates feeding in the rat. Hypofunctioning of histaminergic transmission has moreover been demonstrated in genetically obese rats (Machidori et al., *Brain Research*, 1992, 590, 180-186). Consequently, eating behaviour disorders and obesity are also potential therapeutic indications for the compounds of the present invention.

The present invention relates to new azabicyclic compounds which are distinguished from the compounds mentioned in Application WO2005/089747 by the presence of a 3-azabicyclo[3.2.0]heptane ring system.

Surprisingly, this structural difference from the compounds of Application WO2005/089747 provides the compounds of the invention not only with remarkable pro-cognitive properties but also with powerful awakening, anti-sedative, anti-hypnotic and anxiolytic properties.

At the neurological level, this combination of activities opens the way not only to new treatments for cognitive disorders associated with cerebral ageing, with neurodegenerative diseases or with cranial traumas but also to the treatment of psycho-behavioural disorders associated with those pathologies, such as sleep disorders, apathy and/or depressive states. The pharmacological profile of the compounds of the invention moreover also makes it possible to envisage new treatments in the psychiatric field, for example for Tourette's syndrome, schizophrenia, mood disorders or sleep disorders.

The present invention relates, more specifically, to compounds of formula (I):

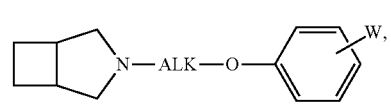

wherein:
ALK represents an alkylene chain,
W represents a group

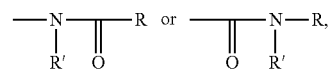

in which R and R', each independently of the other, represent a hydrogen atom or a linear or branched ($C_1$-$C_6$) alkyl group optionally substituted by one or more groups selected from halogen, hydroxy and alkoxy, it being understood that:
the term "alkylene" denotes a linear or branched divalent radical containing from 2 to 6 carbon atoms,
the term "alkoxy" denotes an alkyl-oxy group in which the alkyl chain, which is linear or branched, contains from 1 to 6 carbon atoms, to their enantiomers and diastereoisomers, and also to addition salts thereof with a pharmaceutically acceptable acid or base.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid etc.

Among the pharmaceutically acceptable bases there may be mentioned, without implying any limitation, sodium hydroxide, potassium hydroxide, triethylamine, tert-butylamine etc.

Compounds of formula (I) to which preference is given are those wherein the W group is located in the para position.

ALK preferably represents a linear divalent radical containing from 2 to 6 carbon atoms such as, for example, an ethylene, propylene or butylene group, more preferably still a propylene group.

A particular embodiment of the invention relates to compounds of formula (I) wherein W represents the group

Another particular embodiment of the invention relates to compounds of formula (I) wherein W represents the group

Advantageously, R and R', each independently of the other, represent a hydrogen atom, a methyl group or an ethyl group, those groups optionally being substituted by a methoxy group.

More especially, W represents a group —CO—NH—CH$_3$, —CO—N(CH$_3$)$_2$, —CO—NH$_2$, —CO—N(CH$_2$CH$_3$)$_2$, —NH—CO—CH$_3$, —N(CH$_3$)—CO—CH$_3$ or —NH—CO—CH$_2$—OCH$_3$.

Compounds of meso configuration are more especially preferred.

Even more especially, the invention relates to the compounds of formula (I) which are:
- 4-{3-[(1R,5S)-3-azabicyclo[3.2.0]hept-3-yl]propoxy}benzamide,
- N-(4-{3-[(1R,5S)-3-azabicyclo[3.2.0]hept-3-yl]propoxy}phenyl)acetamide,
- 4-{3-[(1R,5S)-3-azabicyclo[3.2.0]hept-3-yl]propoxy}-N,N-dimethylbenzamide,
- N-(4-{3-[(1R,5S)-3-azabicyclo[3.2.0]hept-3-yl]propoxy}phenyl)-N-methyl-acetamide, and addition salts thereof with a pharmaceutically acceptable acid or base.

Among the addition salts with a pharmaceutically acceptable acid, preference is given more especially to hydrochlorides, oxalates and citrates.

The invention relates also to a process for the preparation of compounds of formula (I), which process is characterised in that there is used as starting material the compound of formula (II):

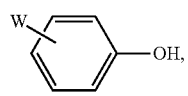

wherein W is as defined for formula (I),
with which compound of formula (II) there is condensed, in a basic medium, the compound of formula (III):

wherein ALK is as defined for formula (I),
to obtain the compound of formula (IV):

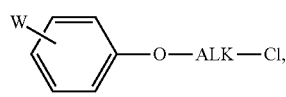

wherein W and ALK are as defined hereinbefore,
with which there is condensed the compound of formula (V):

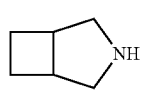

to yield the compound of formula (I) as defined hereinbefore:

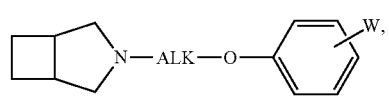

which may be purified according to a conventional separation technique, is converted, if desired, into its addition salts with a pharmaceutically acceptable acid or base and is separated, where appropriate, into its optical isomers according to a conventional separation technique.

The compounds of formulae (II), (III) and (V) are either commercially available or can be obtained by the person skilled in the art using conventional chemical reactions described in the literature.

Alternatively, compounds of formula (VI):

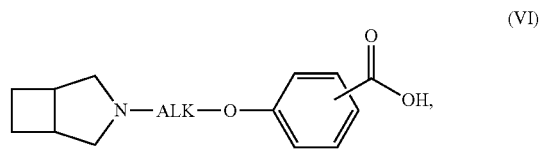

wherein the ALK group is as defined hereinbefore,
can be used as synthesis intermediates for compounds of formula (I/a), particular cases of compounds of formula (I), wherein W represents a —CONRR' group, by coupling with an amine of formula NHRR', wherein R and R' are as defined for formula (I).

Similarly, compounds of formula (VII):

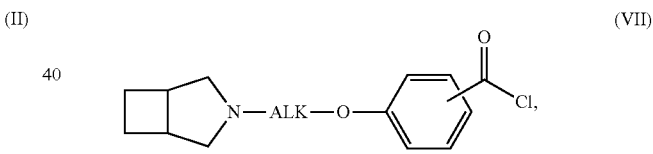

wherein the ALK group is as defined hereinbefore,
can be used as synthesis intermediates for compounds of formula (I/a), particular cases of compounds of formula (I), wherein W represents a —CONRR' group, by coupling with an amine of formula NHRR', wherein R and R' are as defined for formula (I).

Furthermore, compounds of formula (I/a), particular cases of compounds of formula (I), wherein W represents a —CONRR' group, may also be obtained by condensation of the amine NHRR', wherein R and R' are as defined for formula (I), using compounds of formula (VIII):

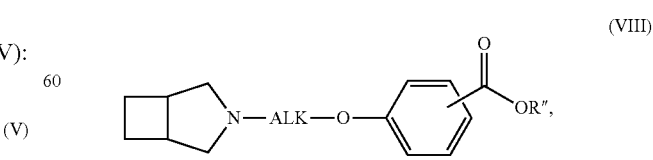

wherein the ALK group is as defined hereinbefore and R" represents a linear or branched (C$_1$-C$_6$)alkyl group or a benzyl group, the compounds of formula (VIII) being prepared via the corresponding carboxylic acid (VI) or acyl chloride (VII) shown hereinbefore.

Finally, it is also possible to obtain compounds of formula (I/a) by hydrolysing compounds of formula (IX):

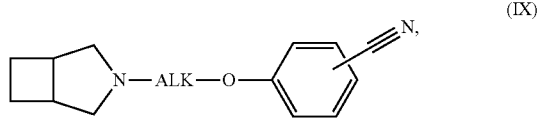

(IX)

wherein the ALK group is as defined hereinbefore.

Pharmacological study of the compounds of formula (I) has shown that they have pro-cognitive properties by means of facilitating processes of memory and learning, and also awakening, anti-sedative, anti-hypnotic and anxiolytic properties.

At the neurological level, the compounds according to the invention may be useful in the treatment of cognitive disorders associated with cerebral ageing or with neurodegenerative diseases such as Alzheimer's disease, Parkinson's disease, Pick's disease, Lewy body dementias, frontal and subcortical dementias, frontotemporal dementias, vascular dementias, Huntington's disease and multiple sclerosis, in new treatments for cognitive disorders associated with cranial traumas, but also in the treatment of psycho-behavioural disorders associated with those pathologies, such as sleep disorders, apathy and anxio-depressive states. Sleep disorders associated with Alzheimer's disease and with Parkinson's disease, such as diurnal hypersomnolence, especially are targets. Furthermore, the motor disorders associated with Parkinson's disease may also be treated by compounds of the present invention.

At the psychiatric level, these compounds may be useful in the treatment of mood disorders, and more especially in the treatment of anxio-depressive states, of Tourette's syndrome, of schizophrenia and of cognitive disorders associated therewith, and of pain, and also in the treatment of sleep disorders, of sleep-waking rhythm disorders and of attention-deficit hyperactivity syndrome (ADHD). Among the sleep disorders there may be more especially mentioned narcolepsy and sleep apnoea. Sleep disorders such as hypersomnia occurring in obstructive sleep apnoea syndrome or in attention-deficit hyperactivity syndrome, and also diurnal somnolence are also targets.

The present invention relates also to pharmaceutical compositions comprising one compound of formula (I) in combination with one or more pharmaceutically acceptable excipients.

In the pharmaceutical compositions according to the invention, the weight proportion of active ingredient (weight of the active ingredient over the total weight of the composition) is from 1 to 50%.

Among the pharmaceutical compositions according to the invention, there may be mentioned more especially those that are suitable for oral, parenteral, nasal, per- or trans-cutaneous, rectal, perlingual, ocular or respiratory administration, especially tablets or dragées, sublingual tablets, sachets, paquets, capsules, glossettes, lozenges, suppositories, creams, ointments, dermal gels, and drinkable or injectable ampoules.

The useful dosage varies according to the sex, age and weight of the patient, the administration route, the nature of the therapeutic indication, and any associated treatments, and ranges from 0.05 mg to 500 mg per 24 hours for treatment in from 1 to 3 administrations per day.

The association of a compound of formula (I) with L-dopa, and more especially still the association of 4-{3-[(1R,5S)-3-azabicyclo[3.2.0]hept-3-yl]propoxy}benzamide, or an addition salt thereof with a pharmaceutically acceptable acid or base, with L-dopa, also forms an integral part of the invention. Associations of this type may be used in the treatment of cognitive and motor disorders of Parkinson's disease.

The following Examples illustrate the invention but do not limit it in any way. The structures of the compounds described in the Examples were determined in accordance with the usual spectrophotometric techniques (infrared, NMR, mass spectrometry etc.).

By way of information, all the compounds hereinbelow have meso type stereochemistry.

EXAMPLE 1

Synthesis Route A

4-{3-[(1R,5S)-3-Azabicyclo[3.2.0]hept-3-yl]-propoxy}benzamide hydrochloride

Step 1: 4-(3-Chloropropoxy)benzamide

A mixture composed of 0.004 mol of 4-hydroxybenzamide, 0.004 mol of 1-bromo-3-chloropropane and 0.006 mol of caesium carbonate in 10 ml of acetonitrile is heated at reflux for 5 hours.

Step 2: 4-{3-[(1R,5S)-3-Azabicyclo[3.2.0]hept-3-yl]propoxy}benzamide

To the reaction mixture of Step 1, at ambient temperature, there are added 0.004 mol of (1R,5S)-3-azabicyclo[3.2.0]heptane, the synthesis of which is described in the publication *J. Med. Chem.* 1967, 10, 621-623, and 0.002 mol of sodium iodide. Heating at reflux is then resumed for 16 hours. The precipitate is filtered off and rinsed with acetonitrile. The filtrate is concentrated to dryness. The residue is taken up in dichloromethane. The resulting solution is extracted with sodium hydroxide solution and then with water, before being dried over magnesium sulphate and concentrated to dryness. The residue is purified by a preparative chromatography technique on a Lichroprep RP-18 phase.

Mass spectrum: $[M+H]^+$ theoretical m/z=275.1760; test m/z=275.1773

Step 3: 4-{3-[(1R,5S)-3-Azabicyclo[3.2.0]hept-3-yl]propoxy}benzamide hydrochloride The product obtained in Step 2 is dissolved in 10 ml of ethanol to which 2 ml of 2N ethereal HCl are added. The product thereby obtained is filtered off, rinsed with ethanol and dried in vacuo.

Elemental Microanalysis:

|  | % C | % H | % N | % Cl⁻ |
|---|---|---|---|---|
| Calculated | 61.83 | 7.46 | 9.01 | 11.41 |
| Found | 61.33 | 7.37 | 8.85 | 11.50 |

EXAMPLE 1

Route B

4-{3-[(1R,5S)-3-Azabicyclo[3.2.0]hept-3-yl]propoxy}benzamide hydrochloride

Step 1: 4-{3-[(1R,5S)-3-Azabicyclo[3.2.0]hept-3-yl]propoxy}benzonitrile

The test procedure is the same as that of Steps 1 and 2 of Example 1, synthesis route A, replacing the 4-hydroxybenzamide in Step 1 by 4-hydroxybenzonitrile.

Step 2: 4-{3-[(1R,5S)-3-Azabicyclo[3.2.0]hept-3-yl]propoxy}benzamide hydrochloride The compound obtained in the Step above (2.2 g) is dissolved in 90 ml of ethanol and heated at reflux in the presence of 5.1 g of KOH for 18 hours. The mixture is poured into 90 ml of water and then concentrated to half volume in vacuo. The solid obtained is filtered off, rinsed with isopropyl ether and then dried. The hydrochloride is prepared in accordance with the procedure of Step 3 of Example 1, synthesis route A.

Elemental Microanalysis:

|  | % C | % H | % N | % Cl⁻ |
| --- | --- | --- | --- | --- |
| Calculated | 61.83 | 7.46 | 9.01 | 11.41 |
| Found | 61.69 | 7.39 | 8.77 | 11.47 |

EXAMPLE 1

Route C

4-{3-[(1R,5S)-3-Azabicyclo[3.2.0]hept-3-yl]propoxy}benzamide hydrochloride

Step 1: Methyl 4-{3-[(1R,5S)-3-azabicyclo[3.2.0]hept-3-yl]propoxy}benzoate

The test procedure is the same as that of Steps 1 and 2 of Example 1, synthesis route A, replacing the 4-hydroxybenzamide in Step 1 by methyl 4-hydroxybenzoate.

Step 2: 4-{3-[(1R,5S)-3-Azabicyclo[3.2.0]hept-3-yl]propoxy}benzoic acid

A mixture of 3.5 g of the compound of Step 1, of 12.7 ml of 2N sodium hydroxide solution and 8 ml of methanol is heated at reflux for one hour. To the reaction mixture, cooled in an ice bath, there are added 12.7 ml of 2N HCl. The precipitate is washed with water and dried in vacuo.

Elemental Microanalysis:

|  | % C | % H | % N |
| --- | --- | --- | --- |
| Calculated | 69.79 | 7.69 | 5.09 |
| Found | 69.67 | 7.73 | 5.44 |

Step 3: 4-{3-[(1R,5S)-3-Azabicyclo[3.2.0]hept-3-yl]propoxy}benzoyl chloride hydrochloride A mixture of 1.8 g of the product described in Step 2 and 20 ml of thionyl chloride is heated at reflux for 2 hours. The reaction mixture is concentrated in vacuo and co-evaporated twice with toluene. The solid residue is homogenised in ethyl ether, filtered and dried in vacuo.

Step 4: 4-{3-[(1R,5S)-3-Azabicyclo[3.2.0]hept-3-yl]propoxy}benzamide hydrochloride To a solution of 1 g of the product described in Step 3 in dichloromethane at 0° C. there are added, dropwise, 4 ml of 2N ammoniacal methanol. The mixture is then stirred for 1 hour at ambient temperature and is washed with 2N sodium hydroxide solution and then with water. The organic phase is dried over magnesium sulphate and concentrated. The residual oil is dissolved in 10 ml of ethanol to which 2 ml of 2N ethereal HCl are added. The product thereby obtained is filtered off, rinsed with ethanol and dried in vacuo.

Elemental Microanalysis:

|  | % C | % H | % N | % Cl⁻ |
| --- | --- | --- | --- | --- |
| Calculated | 61.83 | 7.46 | 9.01 | 11.41 |
| Found | 61.57 | 7.40 | 8.71 | 11.53 |

EXAMPLE 2

4-{3-[(1R,5S)-3-Azabicyclo[3.2.0]hept-3-yl]propoxy}benzamide

The test procedure repeats Steps 1 and 2 of Example 1, synthesis route A.

Elemental Microanalysis:

|  | % C | % H | % N |
| --- | --- | --- | --- |
| Calculated | 70.04 | 8.08 | 10.21 |
| Found | 69.24 | 7.58 | 9.76 |

EXAMPLE 3

4-{2-[(1R,5S)-3-Azabicyclo[3.2.0]hept-3-yl]ethoxy}benzamide

The test procedure is the same as Steps 1 and 2 of Example 1, synthesis route A, replacing the 1-bromo-3-chloropropane in Step 1 by 1-bromo-2-chloroethane.

Elemental Microanalysis:

|  | % C | % H | % N |
| --- | --- | --- | --- |
| Calculated | 69.21 | 7.74 | 10.76 |
| Found | 69.00 | 7.72 | 10.58 |

EXAMPLE 4

4-{4-[(1R,5S)-3-Azabicyclo[3.2.0]hept-3-yl]butoxy}benzamide

The test procedure is the same as Steps 1 and 2 of Example 1, synthesis route A, replacing the 1-bromo-3-chloropropane in Step 1 by 1-bromo-4-chlorobutane.

Elemental Microanalysis:

|  | % C | % H | % N |
|---|---|---|---|
| Calculated | 70.80 | 8.39 | 9.71 |
| Found | 69.18 | 8.28 | 9.37 |

EXAMPLE 5

N-(4-{3-[(1R,5S)-3-azabicyclo[3.2.0]hept-3-yl]propoxy}phenyl)acetamide

The test procedure is the same as Steps 1 and 2 of Example 1, synthesis route A, replacing the 4-hydroxybenzamide in Step 1 by N-(4-hydroxyphenyl)acetamide.

Elemental Microanalysis:

|  | % C | % H | % N |
|---|---|---|---|
| Calculated | 70.80 | 8.39 | 9.71 |
| Found | 70.54 | 8.35 | 10.22 |

EXAMPLE 6

N-(4-{2-[(1R,5S)-3-azabicyclo[3.2.0]hept-3-yl]ethoxy}phenyl)acetamide

The test procedure is the same as Example 3, replacing the 4-hydroxybenzamide by N-(4-hydroxyphenyl)acetamide.

Elemental Microanalysis:

|  | % C | % H | % N |
|---|---|---|---|
| Calculated | 70.04 | 8.08 | 10.21 |
| Found | 69.44 | 7.96 | 9.96 |

EXAMPLE 7

N-(4-{4-[(1R,5S)-3-Azabicyclo[3.2.0]hept-3-yl]butoxy}phenyl)acetamide

The test procedure is the same as Example 4, replacing the 4-hydroxybenzamide by N-(4-hydroxyphenyl)acetamide.

Elemental Microanalysis:

|  | % C | % H | % N |
|---|---|---|---|
| Calculated | 71.49 | 8.67 | 9.26 |
| Found | 71.02 | 8.58 | 8.93 |

EXAMPLE 8

4-{3-[(1R,5S)-3-Azabicyclo[3.2.0]hept-3-yl]propoxy}-N,N-dimethyl-benzamide hydrochloride The test procedure is the same as that of Example 1, synthesis route A, replacing the 4-hydroxybenzamide in Step 1 by 4-hydroxy-N,N-dimethylbenzamide.

Elemental Microanalysis:

|  | % C | % H | % N | % Cl⁻ |
|---|---|---|---|---|
| Calculated | 63.80 | 8.03 | 8.27 | 10.46 |
| Found | 63.29 | 7.95 | 8.19 | 10.50 |

EXAMPLE 9

4-{2-[(1R,5S)-3-Azabicyclo[3.2.0]hept-2-yl]ethoxy}-N,N-dimethyl-benzamide hydrochloride The test procedure is the same as Example 3, replacing the 4-hydroxybenzamide by 4-hydroxy-N,N-dimethylbenzamide. The compound thereby obtained is converted into the salt in accordance with the procedure of Step 3 of Example 1, synthesis route A.

Elemental Microanalysis:

|  | % C | % H | % N | % Cl | % Cl⁻ |
|---|---|---|---|---|---|
| Calculated | 62.86 | 7.76 | 8.62 | 10.91 | 10.91 |
| Found | 62.54 | 7.66 | 8.40 | 10.66 | 10.67 |

EXAMPLE 10

4-{4-[(1R,5S)-3-Azabicyclo[3.2.0]hept-3-yl]butoxy}-N,N-dimethyl-benzamide hydrochloride The test procedure is the same as Example 4, replacing the 4-hydroxybenzamide by 4-hydroxy-N,N-dimethylbenzamide. Then 2 ml of 2N hydrochloric acid are added to the compound thereby obtained in 10 ml of ethanol. The product obtained is filtered off, rinsed with ethyl ether and dried in vacuo.

Elemental Microanalysis:

|  | % C | % H | % N | % Cl⁻ |
|---|---|---|---|---|
| Calculated | 64.67 | 8.28 | 7.94 | 10.05 |
| Found | 64.39 | 7.76 | 7.94 | 10.62 |

EXAMPLE 11

4-{3-[(1R,5S)-3-Azabicyclo[3.2.0]hept-3-yl]propoxy}-N,N-diethyl-benzamide hydrochloride The test procedure is the same as that of Example 1, synthesis route A, replacing the 4-hydroxybenzamide in Step 1 by 4-hydroxy-N,N-diethylbenzamide.

Elemental Microanalysis:

|  | % C | % H | % N | % Cl | % Cl⁻ |
|---|---|---|---|---|---|
| Calculated | 65.47 | 8.52 | 7.63 | 9.66 | 9.66 |
| Found | 64.66 | 8.25 | 7.59 | 10.56 | 10.13 |

EXAMPLE 12

4-{2-[(1R,5S)-3-Azabicyclo[3.2.0]hept-3-yl]ethoxy}-N,N-diethyl-benzamide hydrochloride The test procedure is the same as Example 3, replacing the 4-hydroxybenzamide by 4-hydroxy-N,N-diethylbenzamide. The compound thereby obtained is converted into the salt in accordance with the procedure of Step 3 of Example 1, synthesis route A.

Elemental Microanalysis:

|  | % C | % H | % N | % Cl⁻ |
|---|---|---|---|---|
| Calculated | 64.67 | 8.28 | 7.94 | 10.05 |
| Found | 64.57 | 7.91 | 8.03 | 9.65 |

EXAMPLE 13

4-{4-[(1R,5S)-3-Azabicyclo[3.2.0]hept-3-yl]butoxy}-N,N-diethyl-benzamide hydrochloride The test procedure is the same as Example 4, replacing the 4-hydroxybenzamide by 4-hydroxy-N,N-diethylbenzamide. Then 2 ml of 2N hydrochloric acid are added to the compound thereby obtained in 10 ml of ethanol. The product obtained is filtered off, rinsed with ethyl ether and then dried in vacuo.

Elemental Microanalysis:

|  | % C | % H | % N | % Cl⁻ |
|---|---|---|---|---|
| Calculated | 66.21 | 8.73 | 7.35 | 9.31 |
| Found | 67.41 | 8.34 | 7.67 | 12.01 |

EXAMPLE 14

4-{3-[(1R,5S)-3-Azabicyclo[3.2.0]hept-3-yl]propoxy}-N-methyl-benzamide hydrochloride The test procedure is the same as that of Example 1, synthesis route A, replacing the 4-hydroxybenzamide in Step 1 by 4-hydroxy-N-methylbenzamide.

Elemental Microanalysis:

|  | % C | % H | % N | % Cl | % Cl⁻ |
|---|---|---|---|---|---|
| Calculated | 62.86 | 7.76 | 8.62 | 10.91 | 10.91 |
| Found | 62.57 | 7.68 | 8.61 | 11.10 | 10.99 |

EXAMPLE 15

4-{2-[(1R,5S)-3-Azabicyclo[3.2.0]hept-2-yl]ethoxy}-N-methylbenzamide

The test procedure is the same as Example 3, replacing the 4-hydroxybenzamide by 4-hydroxy-N-methylbenzamide.

Elemental Microanalysis:

|  | % C | % H | % N |
|---|---|---|---|
| Calculated | 70.04 | 8.08 | 10.21 |
| Found | 69.66 | 7.98 | 10.12 |

EXAMPLE 16

4-{4-[(1R,5S)-3-Azabicyclo[3.2.0]hept-3-yl]butoxy}-N-methylbenzamide

The test procedure is the same as Example 4, replacing the 4-hydroxybenzamide by 4-hydroxy-N-methylbenzamide.

Elemental Microanalysis:

|  | % C | % H | % N |
|---|---|---|---|
| Calculated | 71.49 | 8.67 | 9.26 |
| Found | 70.99 | 8.47 | 8.40 |

EXAMPLE 17

N-(4-{3-[(1R,5S)-3-azabicyclo[3.2.0]hept-3-yl]propoxy}phenyl)-N-methylacetamide hydrochloride The test procedure is the same as that of Example 1, synthesis route A, replacing the 4-hydroxybenzamide in Step 1 by N-(4-hydroxyphenyl)-N-methylacetamide.

Elemental Microanalysis:

|  | % C | % H | % N | % Cl | % Cl⁻ |
|---|---|---|---|---|---|
| Calculated | 63.80 | 8.03 | 8.27 | 10.46 | 10.46 |
| Found | 64.07 | 7.97 | 7.88 | 10.16 | 10.30 |

EXAMPLE 18

N-(4-{2-[(1R,5S)-3-azabicyclo[3.2.0]hept-2-yl]ethoxy}phenyl)-N-methylacetamide hydrochloride The test procedure is the same as Example 3, replacing the 4-hydroxybenzamide by N-(4-hydroxyphenyl)-N-methylacetamide. The compound thereby obtained is converted into the salt in accordance with the procedure of Step 3 of Example 1, synthesis route A.

Elemental Microanalysis:

|  | % C | % H | % N | % Cl | % Cl⁻ |
|---|---|---|---|---|---|
| Calculated | 62.86 | 7.76 | 8.62 | 10.91 | 10.91 |
| Found | 62.14 | 7.86 | 8.06 | 11.32 | 10.73 |

EXAMPLE 19

N-(4-{4-[(1R,5S)-3-azabicyclo[3.2.0]hept-3-yl]butoxy}phenyl)-N-methylacetamide hydrochloride The test procedure is the same as Example 13, replacing the 4-hydroxy-N,N-diethylbenzamide by N-(4-hydroxyphenyl)-N-methylacetamide.

Elemental Microanalysis:

|  | % C | % H | % N | % Cl | % Cl⁻ |
|---|---|---|---|---|---|
| Calculated | 64.67 | 8.28 | 7.94 | 10.05 | 10.05 |
| Found | 64.25 | 7.79 | 7.89 | 10.47 | 10.14 |

EXAMPLE 20

N-(4-{3-[(1R,5S)-3-azabicyclo[3.2.0]hept-3-yl]propoxy}phenyl)-2-methoxyacetamide The test procedure is the same as Steps 1 and 2 of Example 1, synthesis route A, replacing the 4-hydroxybenzamide in Step 1 by N-(4-hydroxyphenyl)-2-methoxyacetamide.

Elemental Microanalysis:

|  | % C | % H | % N |
|---|---|---|---|
| Calculated | 67.90 | 8.23 | 8.80 |
| Found | 67.88 | 8.22 | 8.97 |

EXAMPLE 21

N-(4-{2-[(1R,5S)-3-azabicyclo[3.2.0]hept-3-yl]ethoxy}phenyl)-2-methoxyacetamide hydrochloride The test procedure is the same as Example 3, replacing the 4-hydroxybenzamide by N-(4-hydroxyphenyl)-2-methoxyacetamide. Then 2 ml of 2N hydrochloric acid are added to the compound thereby obtained in 10 ml of ethanol. The product obtained is filtered off, rinsed with ethyl ether and then dried in vacuo.

Elemental Microanalysis:

|  | % C | % H | % N | % Cl | % Cl⁻ |
|---|---|---|---|---|---|
| Calculated | 59.91 | 7.39 | 8.22 | 10.40 | 10.40 |
| Found | 59.76 | 7.44 | 8.12 | 10.66 | 10.36 |

EXAMPLE 22

N-(4-{4-[(1R,5S)-3-azabicyclo[3.2.0]hept-3-yl]butoxy}phenyl)-2-methoxyacetamide hydrochloride The test procedure is the same as Example 13, replacing the 4-hydroxy-N,N-diethylbenzamide by N-(4-hydroxyphenyl)-2-methoxyacetamide.

Elemental Microanalysis:

|  | % C | % H | % N | % Cl | % Cl⁻ |
|---|---|---|---|---|---|
| Calculated | 61.86 | 7.92 | 7.59 | 9.61 | 9.61 |
| Found | 61.61 | 7.83 | 7.42 | 9.80 | 9.41 |

EXAMPLE 23

4-{3-[(1R,5S)-3-Azabicyclo[3.2.0]hept-3-yl]propoxy}benzamide oxalate

The test procedure repeats Steps 1 and 2 of Example 1, synthesis route A. Then 0.32 g of oxalic acid is added to 0.38 g of the compound thereby obtained in 6 ml of ethanol. The product obtained is filtered off, rinsed with ethyl ether and then dried in vacuo.

Elemental Microanalysis.

|  | % C | % H | % N |
|---|---|---|---|
| Calculated | 59.33 | 6.64 | 7.69 |
| Found | 58.99 | 6.61 | 7.49 |

EXAMPLE 24

4-{3-[(1R,5S)-3-Azabicyclo[3.2.0]hept-3-yl]propoxy}benzamide citrate

One equivalent of the compound of Example 1, synthesis route A, Step 2, in the presence of 1.2 equivalents of citric acid monohydrate, is dissolved in water to yield the title product.

Elemental Microanalysis:

|  | % C | % H | % N |
|---|---|---|---|
| Calculated | 56.65 | 6.48 | 6.01 |
| Found | 56.49 | 6.60 | 5.99 |

Pharmacological Study

EXAMPLE A

Cerebral Levels of $N^\tau$-Methylhistamine in the NMRI Mouse

The purpose of this study, which was carried out in accordance with the method of Taylor et al. (Biochem. Pharm., 1992, 44, 1261-1267), is to evaluate the ex vivo activity of the compounds of the present invention as antagonists of type $H_3$ central histamine receptors. That activity is revealed by measuring, after treatment with the test compounds by the oral route, the central levels of $N^\tau$-methylhistamine, which is a main metabolite of histamine. An increase in the cerebral concentrations of $N^\tau$-methylhistamine indicates an increase in the turn-over of histamine by blockage of the type $H_3$ central histamine receptors.

NMRI mice (18-20 g) are treated with compounds of the present invention or with their carrier (20 ml/kg) by the oral route. One hour after the pharmacological treatment, the animals are sacrificed; the brains are removed, frozen in liquid nitrogen, weighed and homogenised in 0.1N $HClO_4$ at 4° C. The homogenised products are centrifuged (15000 g, 17 minutes, 4° C.). The supernatants are recovered and divided into aliquots. The aliquots are frozen in liquid nitrogen and stored at −80° C. until they are analysed.

Determination of the cerebral levels of $N^\tau$-methylhistamine is carried out by capillary electrophoresis. The tissue levels of $N^\tau$-methylhistamine are expressed in μg/g of fresh brain. The comparison of the cerebral levels of $N^\tau$-methylhistamine between animals treated with the carrier (controls) and animals treated with compounds of the present invention is carried out by single-factor variance analysis followed, if necessary, by a complementary analysis (Dunnett's test).

The results show that, at a dose of 3 mg/kg PO, the compounds of the present invention are capable of significantly increasing endogenous cerebral concentrations of $N^\tau$-methyl-histamine. Accordingly, the compounds of Examples 1, 5, 8 and 17 increase the cerebral concentrations of $N^\tau$-methyl-histamine by more than 100%.

EXAMPLE B

Electroencephalogram Recordings in the Awake Wistar Rat

Electrodes are chronically implanted in adult male Wistar rats, being located at the surface of the frontal and parietal cortex. Cortical electroencephalogram (EEG) recordings are made in the rats placed in cages in a sound-proofed room. The compounds and carriers are administered in randomised manner by the intraperitoneal route at 10 o'clock on the same days with a minimum of 3 days between each administration, allowing each rat to be used as its own control. The absolute power of the slow delta activities (1-4 Hz), which predominate during slow sleep and disappear during wakefulness and paradoxical sleep, is averaged over successive periods of 30 minutes. Over 30 minutes, high and low values for the power of the slow delta activities are signs of wakefulness and of sleep, respectively.

The results show that the compounds of the present invention increase cortical wakefulness (reduction in delta waves) in the rat.

By way of example, the compound of Example 1, administered at a dose of 3 mg/kg IP, causes a significant reduction in the power of the slow delta waves for 120 minutes, a sign of cortical activation and wakefulness.

EXAMPLE C

Interaction with Barbital in the Wistar Rat

The objective of this test is to determine the anti-sedative, awakening and/or anti-hypnotic properties of the compounds of the present invention. The rats are placed in individual cages and are given an injection of barbital (170 mg/kg IP). The duration of sleep is then measured for 4 hours after the injection of barbital, determined on the basis of loss of the righting reflex. The compounds of the invention or their carriers are administered by the oral route 30 minutes before the administration of barbital. The results demonstrate that the compounds of the present invention have powerful anti-sedative, anti-hypnotic and/or awakening activities.

For example, at a dose of 10 mg/kg PO, the compound of Example 1 reduces the duration of sleeping caused by the barbital by −81%.

EXAMPLE D

Object Recognition in the Sprague-Dawley Rat

The object recognition test in the Sprague-Dawley rat (Behav. Brain Res., 1988, 31, 47-59) is based on the spontaneous exploratory activity of the animal and has the characteristics of episodic memory in humans. This memory test is sensitive to ageing (Eur. J. Pharmacol., 1997, 325, 173-180) and to cholinergic dysfunctions (Pharm. Biochem. Behav. 1996, 53(2), 277-283) and is based on the differences in the exploration of 2 objects of fairly similar shape—one familiar, the other new. Prior to the test, the animals are habituated to the environment (an enclosure without an object). In the course of a first session, the rats are placed (3 minutes) in the enclosure, in which there are 2 identical objects. The duration of exploration is measured for each object. In the course of the second session (3 minutes), 24 hours later, 1 of the 2 objects is replaced by a new object. The duration of exploration is measured for each object. The assessment criterion is the difference, Delta, expressed in seconds, between the exploration times for the new object and for the familiar object in the course of the second session. The control animals, previously treated with the carrier by the oral route 60 minutes before each session, explore the familiar object and the new object in an identical manner, which indicates that the object introduced earlier has been forgotten. Animals treated with a compound that facilitates mnemocognition preferentially explore the new object, which indicates that the object introduced earlier has been remembered.

For Example, the results obtained with Example 1 of the present invention show a difference, Delta, of the order of 8 seconds, at a dose of 3 mg/kg PO, which shows that the compounds of the invention greatly enhance memorisation, even at a low dose.

EXAMPLE E

Social Recognition in the Wistar Rat

Initially described in 1982 (J. Comp. Physiol., 1982, 96, 1000-1006), the social recognition test has subsequently been proposed by various authors (Psychopharmacology, 1987, 91, 363-368; Psychopharmacology, 1989, 97, 262-268) for studying the mnemocognitive effects of new compounds. The test is based on the natural expression of the olfactory memory of the rat and its natural tendency to forget and allows evaluation of memorisation, by recognition of a young congeneric animal, by an adult rat. A young rat (21 days), taken at random, is placed for 5 minutes in the cage housing an adult rat. With the aid of a video device, the experimenter observes the social recognition behaviour of the adult rat and measures its overall duration. The young rat is then removed from the adult rat's cage and is placed in its own cage until the second introduction. The adult rat is given the compound under test by the intraperitoneal route and, after 2 hours, is again brought into the presence (5 minutes) of the young rat. The social recognition behaviour is then observed again and its duration measured. The assessment criterion is the difference (T2–T1), expressed in seconds, between the "recognition" times of the 2 encounters.

The results obtained with Example 1 show a difference (T2–T1) of 24 seconds and of 36 seconds for doses of 1 and 3 mg/kg IP, respectively, which shows that the compounds of the invention very greatly enhance memorisation, even at a low dose.

EXAMPLE F

Tail Suspension Test in the NMRI Mouse

The tail suspension test in the mouse (Porsolt et al., *Arch. Int. Pharmacodyn.*, 1987, 288, 11) enables detection of psychopharmacological properties of compounds. NMRI mice are suspended by the tail, with the aid of a piece of adhesive tape, from a hook for 6 minutes: the immobility time is measured automatically with the aid of movement sensors. The animals are treated, by the intraperitoneal route, with the compounds of the invention or their carriers 24 hours and 30 minutes before they are suspended.

The results show that Example 1, when administered at a dose of 10 mg/kg IP, causes an increase in the immobility time of 119%. This result indicates that the compounds of the present invention have anxiolytic properties.

EXAMPLE G

Intracerebral Microdialysis in the Striatum of the Awake Rat

Intracerebral microdialysis in the awake rat makes it possible to assess the influence of a compound on the release of neurotransmitters such as dopamine into the extracellular space of small cerebral structures, especially the striatum.

This technique is carried out in two steps: a surgery step (stereotaxic implantation of a cannula-guide carried out on the anaesthetised animal) and a microdialysis step carried out on the awake animal (collection of samples of extracellular cerebral liquid). Male rats of the Wistar strain (280-320 g) are anaesthetised and placed in a stereotaxic apparatus. A guide cannula is implanted in the striatum of the animals according to the following stereotaxic coordinates: antero-posteriority –1 mm, laterality +2.8 mm, depth –3 mm, relative to the bregma, according to the atlas of Paxinos and Watson (1996). One week after the surgery, a microdialysis probe (CMA11, length 4 mm, Phymep) is inserted into the guide cannula. The animals are placed in experimentation cages and the to probe inlet is connected to a pump continuously perfusing artificial cerebrospinal fluid (flow rate 1 μl/min). After a stabilisation period of 2 hours, collection of the microdialysates is started. Samples are collected under baseline conditions (4 samples) and then after intraperitoneal administration of the compound (6 post-treatment samples). The extracellular levels of dopamine are assessed in each microdialysate using a liquid chromatographic technique coupled with electrochemical detection. The values are expressed as the mean±SEM relative to the baseline values (reference 100%). The results show that Example 1 of the present invention is capable of significantly increasing the endogenous cerebral concentrations of dopamine of +123% (in comparison with basal values) at a dose of 10 mg/kg i.p.

EXAMPLE H

Pharmaceutical Compositions

Formula for the preparation of 1000 tablets each containing 100 mg of active ingredient:

| | |
|---|---|
| Compound of Example 1 | 100 g |
| Hydroxypropylcellulose | 20 g |
| Polyvinylpyrrolidone | 20 g |
| Wheat starch | 150 g |
| Lactose | 900 g |
| Magnesium stearate | 30 g |

The invention claimed is:

1. A compound selected from those of formula (I):

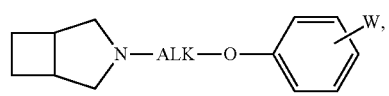

wherein:
ALK represents an alkylene chain,
W represents

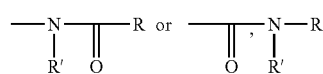

in which R and R', each independently of the other, represent a hydrogen atom or a linear or branched ($C_1$-$C_6$) alkyl group optionally substituted by one or more groups selected from halogen, hydroxy and alkoxy,
it being understood that:
the term "alkylene" means a linear or branched divalent radical having from 2 to 6 carbon atoms,
the term "alkoxy" means an alkyl-oxy group in which the alkyl chain, which is linear or branched, has from 1 to 6 carbon atoms,
its enantiomers, diastereoisomers, and addition salts thereof with a pharmaceutically acceptable acid or base.

2. The compound of claim 1, wherein the W group is located in the para position.

3. The compound of claim 1, wherein ALK represents a linear divalent radical having from 2 to 4 carbon atoms.

4. The compound of claim 1, wherein ALK represents a propylene group.

5. The compound of claim 1, wherein W represents

6. The compound of claim 1, wherein W represents

7. The compound of claim 1, wherein R and R', each independently of the other, represent a hydrogen atom, a methyl group or an ethyl group, wherein the methyl group or the ethyl group is optionally substituted by a methoxy group.

8. The compound of claim 1, wherein W represents —CO—NH$_2$, —CO—NH—CH$_3$, —CO—N(CH$_3$)$_2$, —CO—N(CH$_2$CH$_3$)$_2$, —NH—CO—CH$_3$, —N(CH$_3$)—CO—CH$_3$ or —NH—CO—CH$_2$—OCH$_3$.

9. The compound of claim 1, which is selected from:
4-{3-[(1R,5S)-3-azabicyclo[3.2.0]hept-3-yl]propoxy}benzamide,
N-(4-{3-[(1R,5S)-3-azabicyclo[3.2.0]hept-3-yl]propoxy}phenyl)acetamide,
4-{3-[(1R,5S)-3-azabicyclo[3.2.0]hept-3-yl]propoxy}-N,N-dimethylbenzamide,
N-(4-{3-[(1R,5S)-3-azabicyclo[3.2.0]hept-3-yl]propoxy}phenyl)-N-methyl-acetamide,
and addition salts thereof with a pharmaceutically acceptable acid or base.

10. The compound of claim 1, which is selected from:
4-{3-[(1R,5S)-3-azabicyclo[3.2.0]hept-3-yl]propoxy}benzamide hydrochloride,
4-{3-[(1R,5S)-3-azabicyclo[3.2.0]hept-3-yl]propoxy}benzamide oxalate, and
4-{3-[(1R,5S)-3-azabicyclo[3.2.0]hept-3-yl]propoxy}benzamide citrate.

11. A compound selected from those of formula (VI):

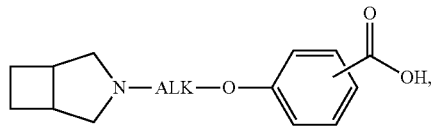

(VI)

wherein ALK represents an alkylene chain.

12. A compound selected from those of formula (VII):

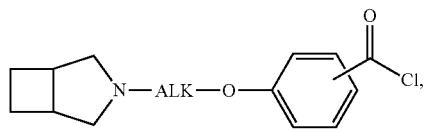

(VII)

wherein ALK represents an alkylene chain.

13. A compound selected from those of formula (VIII):

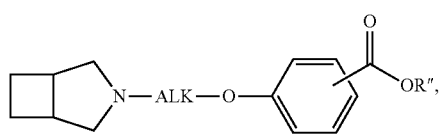

(VIII)

wherein ALK represents an alkylene chain and R″ represents a linear or branched (C$_1$-C$_6$)alkyl group or a benzyl group.

14. A compound selected from those of formula (IX):

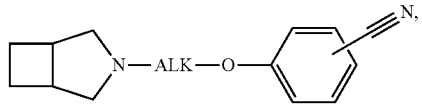

(IX)

wherein ALK represents an alkylene chain.

15. A pharmaceutical composition comprising as active ingredient a compound of claim 1, or an addition salt thereof with a pharmaceutically acceptable acid or base, in combination with one or more pharmaceutically acceptable excipients.

16. A method of treating a condition selected from cognitive and psycho-behavioural disorders associated with cerebral ageing, with neurodegenerative diseases or with cranial traumas in a subject in need thereof, comprising administration of an effective amount of a compound of claim 1.

17. The method of claim 16 wherein the condition is selected from cognitive and psycho-behavioural disorders associated with Alzheimer's disease, Parkinson's disease, Pick's disease, Lewy body dementias, frontal and subcortical dementias, frontotemporal dementias, vascular dementias, Huntington's disease and/or multiple sclerosis.

18. The method of claim 16 wherein the condition is a psycho-behavioural disorder selected from sleep disorders, apathy and anxio-depressive states.

19. The method of claim 18 wherein the condition is selected from sleep disorders associated with Alzheimer's disease and with Parkinson's disease.

20. A method of treating motor disorders associated with Parkinson's disease in a subject in need thereof, comprising administration of an effective amount of a compound of claim 1.

21. A method of treating a condition selected from mood disorders, anxio-depressive states, Tourette's syndrome, schizophrenia, and cognitive disorders associated therewith, pain, sleep disorders, sleep-waking rhythm disorders, and attention-deficit hyperactivity syndrome in a subject in need thereof, comprising administration of an effective amount of a compound of claim 1.

22. The method of claim 21 wherein the sleep disorder is selected from narcolepsy, hypersomnia occurring in obstructive sleep apnoea syndrome, hypersomnia occurring in attention-deficit hyperactivity syndrome, and diurnal somnolence.

23. A composition comprising a compound of claim 1 in combination with L-dopa.

24. A method of treating cognitive and motor disorders of Parkinson's disease in a subject in need thereof, comprising administration of an effective amount of a composition of claim 23.

* * * * *